United States Patent [19]

Haugwitz et al.

[11] 4,138,493
[45] Feb. 6, 1979

[54] 2,2-DIHALO-1(3)-LOWER ALKYL-CYCLOPROPYLALKYLTHIO BENZIMIDAZOLE DERIVATIVES, COMPOSITIONS THEREOF AND METHOD OF USE IN TREATING TAPEWORMS AND WHIPWORMS

[75] Inventors: Rudiger D. Haugwitz, Titusville; Larry R. Cruthers, Flemington; Barbara V. Maurer, Titusville, all of N.J.

[73] Assignee: E. R. Squibb & Sons, Inc., Princeton, N.J.

[21] Appl. No.: 885,717

[22] Filed: Mar. 13, 1978

[51] Int. Cl.² .................. A61K 31/415; C07D 235/32
[52] U.S. Cl. ................................. 424/273 B; 548/306
[58] Field of Search ................ 424/273 R, 273 B; 548/306

[56] References Cited
U.S. PATENT DOCUMENTS 4,046,908  9/1977  Haugwitz ...................... 424/273 R Primary Examiner—Sam Rosen Attorney, Agent, or Firm—Lawrence S. Levinson; Merle J. Smith; Burton Rodney

[57] ABSTRACT

Benzimidazole derivatives are provided having the structure

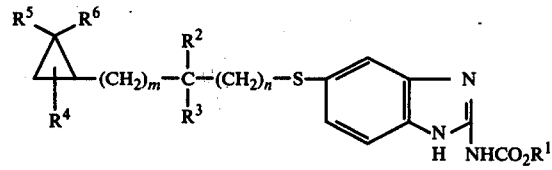

wherein $R^1$ is lower alkyl or phenyl-lower alkyl, $R^2$ and $R^3$ are the same or different and are hydrogen or lower alkyl, $R^4$ is lower alkyl or phenyl, and $R^5$ and $R^6$ are the same or different and are chlorine, bromine, fluorine or iodine, m is 0 to 3, n is 0 to 3, and m + n is $\leq$ 5, and physiologically acceptable salts thereof. These compounds are especially useful in treating or preventing tapeworm and whipworm infestation in mammalian species or poultry.

15 Claims, No Drawings

2,2-DIHALO-1(3)-LOWER ALKYL-CYCLOPROPYLALKYLTHIO BENZIMIDAZOLE DERIVATIVES, COMPOSITIONS THEREOF AND METHOD OF USE IN TREATING TAPEWORMS AND WHIPWORMS

BACKGROUND OF THE INVENTION

U.S. Pat. No. 4,025,638 to Gyurik discloses 5-cycloalkylthio- or oxy-2-carbalkoxyaminobenzimidazoles wherein the cycloalkyl is unsubstituted. These compounds are said to be generally useful for their anthelmintic properties.

U.S. Pat. No. 4,046,908 to Haugwitz et al discloses compounds of the structure

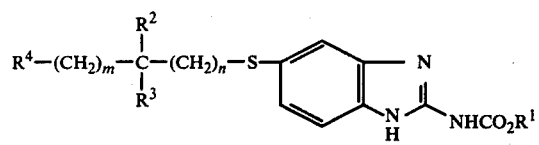

wherein $R^1$ is lower alkyl, phenyl-lower alkyl, halo-lower alkyl, mono-lower alkylaminoalkyl, di-lower alkylaminoalkyl, and alkyl pyridinium halide, $R^2$ and $R^3$ may be the same or different and are hydrogen or lower alkyl, $R^4$ is cycloalkyl or cycloalkenyl which may include 1, 2, 3 or 4 halogen or lower alkyl substituents, and m is 0 to 3, n is 0 to 3, and m + n $\leq$ 5, for their use as anthelmintic agents.

In addition, other benzimidazole compounds are known for their use as anthelmintic agents. For example, U.S. Pat. No. 3,574,845 to Actor et al, assigned to Smith Kline, discloses 5(6)-benzene ring substituted benzimidazole-2-carbamate derivatives including 5(6)-methylthio-2-carboethoxyaminobenzimidazole and various 5(6)-alkyl-2-carbomethoxyaminobenzimidazoles;

U.S. Pat. Nos. 3,929,821 and 4,002,640 to Beard et al and assigned to Syntex discloses various 5(6)-benzene ring substituted benzimidazole-2-carbamate derivatives including 5(6)-aralkylthio-2-carbomethoxyaminobenzimidazoles, such as, 5(6)-phenethylthio-2-carbomethoxyaminobenzimidazole.

U.S. Pat. Nos. 3,954,791 to Loewe et al and 3,928,375 to Duwel et al, disclose 2-carbalkoxy-amino-benzimidazole-5(6-phenyl and phenylthio ethers.

Other benzimidazoles useful as anthelmintic agents are disclosed in U.S. Pat. Nos. 3,929,822, 3,929,823, 3,929,824, 3,935,209, 3,965,113 and 4,005,202 all to Beard et al and assigned to Syntex; U.S. Pat. Nos. 3,682,952 to Actor et al, 3,578,676 and 3,694,455 to Dunn, 3,915,986 and 3,969,526 to Gyurik, all assigned to Smith Kline; and U.S. Pat. No. 3,738,993 to Haugwitz et al, assigned to Squibb.

DESCRIPTION OF THE INVENTION

It has now been found that the benzimidazole compounds of the invention which include a 5-dihalo-1-lower alkyl-cyclopropyl alkylenethio substituent are surprisingly useful in treating, inhibiting or preventing tapeworm and/or whipworm infestation in mammalian species, such as dogs, horses, pigs, cats, cattle, sheep, mice, and poultry, such as chickens, turkeys, geese and the like.

The 5-dihalo-1(3)-lower alkyl-cyclopropyl alkylenethio benzimidazole carbamates of the invention have the following structure

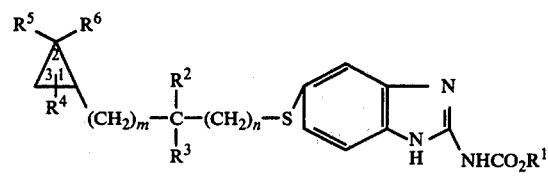

wherein $R^1$ is lower alkyl or phenyl-lower alkyl, $R^2$ and $R^3$ are the same or different and are hydrogen or lower alkyl, $R^4$ occupies the 1- or 3-position and is lower alkyl or phenyl, and $R^5$ and $R^6$ are the same or different and are chlorine, bromine, fluorine or iodine, m is 0 to 3, n is 0 to 3, and m + n is $\leq$ 5.

A method is also provided for treating or preventing whipworm, tapeworm and other helminth infestation by orally, parenterally or topically administering to a mammalian or poultry host a benzimidazole as described above.

The term "lower alkyl" as used herein includes straight or branched chain aliphatic hydrocarbon radicals having up to and including seven carbon atoms, such as methyl, ethyl, propyl, isopropyl, n-butyl, isobutyl, t-butyl, amyl, hexyl, heptyl and the like. Preferred lower alkyl groups contain from 1 to 4 carbon atoms.

$(CH_2)_m$ and $(CH_2)_n$ represent a single bond or straight or branched chain alkylene radicals containing 3 or less carbons in the longest normal chain.

Preferred are those benzimidazoles wherein $R^5$ and $R^6$ are chlorine and/or bromine, $R^4$ is methyl or ethyl in the 1-position,

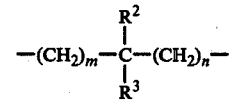

is methylene or ethylene, and $R^1$ is methyl or benzyl

The benzimidazole derivatives of structure I may be prepared by thiocyanation of o-nitroaniline to yield 4-thiocyano-2-nitroaniline (II). This product is then subjected to a sodium borohydride reduction to yield the corresponding 4-mercapto-2-nitroaniline (III). The mercapto derivative may be isolated or used directly for the next step. Thus, to the reaction mixture there is added the haloalkyl cycloalkane IV to furnish the sulfide V.

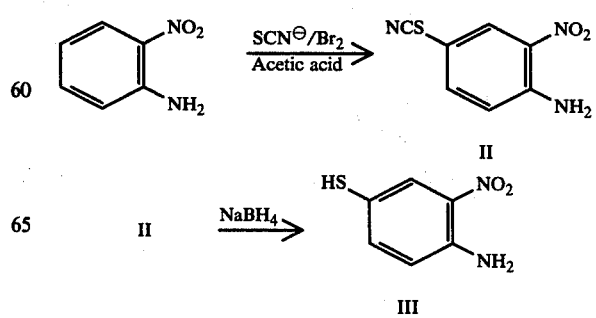

III + 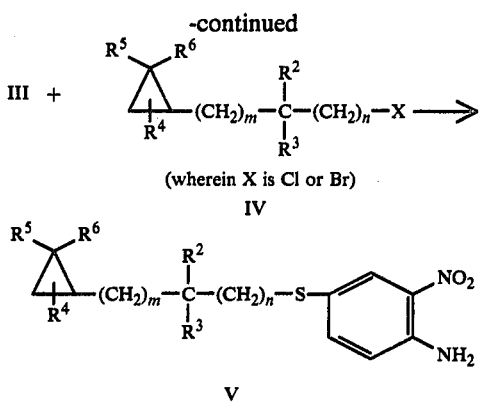 →

(wherein X is Cl or Br)
IV

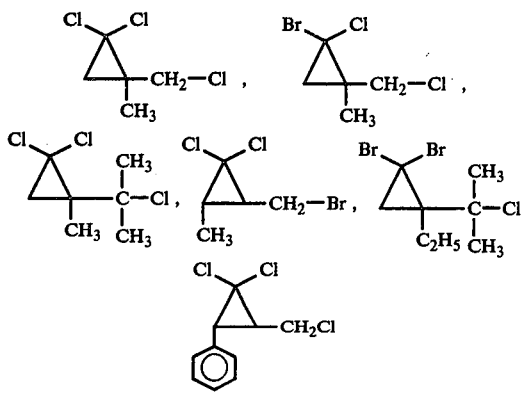

V

Examples of haloalkyl cycloalkanes of formula IV suitable for use herein include the following:

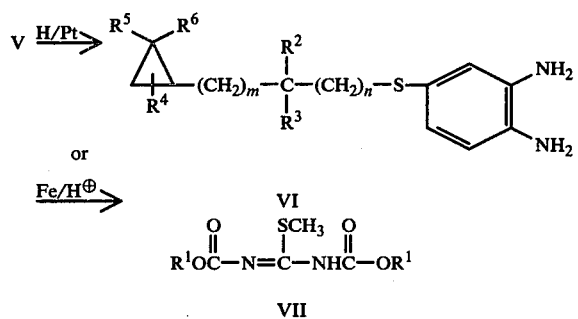

The resulting sulfides V may be purified by crystallization and then reduced to the corresponding o-phenylene diamine VI. Either chemical or catalytic reduction may be used. For the chemical reduction the procedure outlined by Sandler and Caro (*Organic Functional Group Preparations,* 1968, pp. 339–340) is preferred. The final step in the synthesis of I, namely ring closure of VI to furnish I, can be achieved in various ways. Whereas refluxing of VI with the isolated thiourea derivative VII in alcohols such as methanol or ethanol will furnish I, the preferred method of preparing I is by forming VII in situ and then without isolating it adding VI and refluxing it for 30 minutes to 5 hours to yield the desired product.

V $\xrightarrow{H/Pt}$ or $\xrightarrow{Fe/H^{\oplus}}$

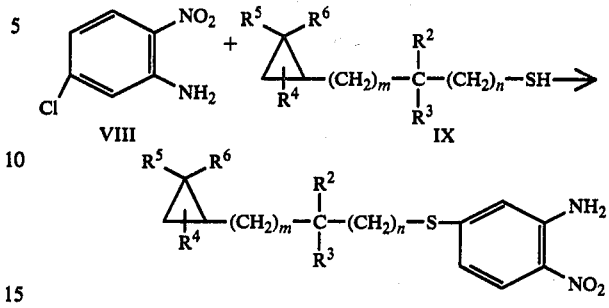

VI $$R^1OC(=O)-N=C(SCH_3)-NHC(=O)-OR^1$$

VII

An alternative route toward the intermediate VI offers the reaction of VIII with the requisite mercaptoalkyl cycloalkane IX, to yield X. Here, in contrast to the alkylation step described above, (i.e., IV → V) the reaction temperature has to be higher and the reaction periods have to be longer. Reduction of X yields the desired diamine VI

VIII + IX →

X

A great variety of haloalkyl cycloalkanes IV are commercially available. In some cases the requisite haloalkyl cycloalkane has to be synthesized. For example, reaction of the appropriate alkene with the requisite halocarbene will yield the desired starting material.

The requisite haloalkyl cycloalkanes may also be prepared from the corresponding alcohols by standard reactions.

In certain instances, the compounds of formula I form physiologically acceptable acid-addition salts with inorganic and organic acids. These salts frequently provide useful means for isolating the products from reaction mixtures by forming the salt in a medium in which it is insoluble. The free base may then be obtained by neutralization. Then any other salt may again be formed from the free base and the appropriate inorganic acid. Illustrative are the hydrohalides, especially the hydrochloride and hydrobromide which are preferred, sulfate, nitrate, tartrate, methanesulfonate, benzenesulfonate, toluenesulfonate, and the like.

In accordance with the present invention, the compounds of formula I are administered orally, parenterally, such as subcutaneously, intravenously, intramuscularly or interperitoneally, or topically (cutaneously), preferably directly on to exposed skin surface, to a host in the treatment and/or prevention of helminthiasis. Helminthiasis is a parasitic disease which causes widespread and often serious infection in domesticated animals, such as swine, horses, cattle, poultry, dogs, cats and sheep. The compounds administered orally, parenterally or topically are useful in treating infections caused by Haemonchus, Ostertagia, Trichostrongylus, Cooperia, Dictyocaulus, Nematodirus, Bunostomum, Strongyloides, Oesophagostomum, Ancylostoma, Uncinaria, Toxocara, Toxascaris, Strongylus, Trichonema spp, Oxyuris, Parascaris, Ascaridia, Heterakis, Capillaria, Ascaris, Metastrongylus, and liver flukes and are particularly useful in treating Trichuris (whipworm) and Moniezia, *Taenia pisiformis, Dipylidium caninum, Anoplocephala* or Raillietina (tapeworms).

When the compounds of formula I are to be administered in unit dosage form, capsules, boluses or drenches containing the desired amount of anthelmintic distributed in a pharmaceutically acceptable vehicle are usually employed. These are prepared by intimately and uniformly mixing the active ingredient with suitable finely divided diluents, suspending agents, fillers, disintegrating agents and/or binders such as starch, lactose, talc, magnesium stearate, vegetable gums and the like are compounded to techniques generally known in the art.

The compounds of formula I may also be administered as a component of the feed of the animals or suspended in the drinking water. Thus, novel feed and feed supplement compositions may be prepared in which the compounds of this invention are present as an active anthelmintic ingredient. A typical feed supplement comprises the anthelmintic agent intimately dispersed in or admixed with an inert carrier or diluent, i.e., one that is nonreactive with respect to the anthelmintic agent and that may be administered with safety to the animals. The carrier or diluent is preferably one that is or may be an ingredient of an animal ration. This composition may be mixed with the feed to give any useful desired concentration, preferably about 0.1–2%. Lastly, feeds containing the active ingredient may be made directly by mixing said active ingredient in a feed which is inert to said anthelmintic compounds so as to give feeds having concentrations of anthelmintic agent of from 0.1–2%.

In preparing injectable compositions, the compounds are mixed with a non-toxic, physiologically acceptable non-pyrogenic carrier such as sterile water, sterile saline solution, benzyl benzoate, 1,3-butylene glycol, ethyl oleate, castor oil, glyceryl triacetate, sesame oil, and sesame oil:benzyl benzoate (1:1). The parenteral product will usually take the form of a suspension containing from about 1 to about 10% by weight of the compound of formula I.

The above injectable compositions may also include a non-toxic physiologically acceptable non-pyrogenic suspending agent. Thus, where a non-oily carrier is employed such as water, suspending agents such as carboxymethyl cellulose, methyl cellulose, polyvinyl pyrrolidone or non-antigenic gelatin may be employed. Where the carrier employed is an oil, aluminum monostearate may be employed as a suspending agent. The suspending agent may be employed in amounts ranging from about 0.05 to about 2%, and preferably from about 0.1 to about 1% by volume of carrier (the above % may be based on the weight of the carrier where the carrier is qs to 100g).

A non-toxic, non-pyrogenic wetting agent may also be included in the injectable compositions in amounts ranging from about 0.005 to about 2% and preferably from about 0.01 to about 0.1% by weight of the carrier. Examples of suitable wetting agents include non-ionic surfactants such as polyoxyethylene sorbitan monostearate, polyoxyethylene sorbitan monooleate [e.g., Tweens] and fatty acid monoglycerides or diglycerides. Other surfactants suitable for use herein are disclosed in the published literature, for example, Kirk-Othmer, Encyclopedia of Chemical Technology, Second Edition, Volume 19, page 507 et seq.

In preparing topical or cutaneous compositions, the anthelmintic compounds are mixed with carriers which are effective in penetrating the skin, whereby the compounds are absorbed by the animal through the skin and transmitted systemically within the animal. A wide range of appropriate carriers may be employed to pass the compound through the skin. The composition employed may be a cream. A liquid composition, however, is particularly convenient to use, e.g., facilitating measuring out doses, and facilitating absorbance through the skin. Thus, a solution or suspension of the compound in a liquid carrier is preferred. Solutions are especially good for transmitting the compound through the skin and are therefore most preferred. The liquid carrier preferably comprises one or more liquids selected from hydrocarbons (e.g., aromatic hydrocarbons, such as an aromatic hydrocarbon fraction of boiling point 130–250° C, e.g., 180–220° C, xylene, benzene or toluene, or paraffins, such as those of 6–20 carbon atoms), halogenated aliphatic hydrocarbons (e.g., carbon tetrachloride), ketones (e.g., cyclohexanone or 2-butanone), esters (e.g., ethyl acetate, ethyl benzoate or triacetin), ethers (e.g., diisopropyl ether or tetrahydrofuran), alcohols (e.g., alkanols of 2–8 carbon atoms, such as butyl alcohol, amyl alcohol or isopropyl alcohol, or glycols, such as monopropylene glycol), amides (e.g., dimethylformamide), sulphones (e.g., dimethyl sulphone or sulpholane), and sulphoxides (e.g., dimethyl sulphoxide). In many cases a mixture of liquids is desirable. Preferably the liquid carrier comprises one or more liquids selected from hydrocarbons (e.g., aromatic hydrocarbons especially xylene), alcohols (e.g., isopropyl alcohol or amyl alcohol and sulphoxides (e.g., dimethyl sulphoxide). Water tends to be ineffective as a liquid carrier for passing the compound through the skin of the animal. Accordingly, the carrier in the liquid compositions preferably comprises an organic liquid.

The viscosity of liquid compositions may be increased over what it would otherwise be by including thickeners which increase the viscosity. This may be desirable in order to retard or prevent the composition from running off the animal.

The additives may include, for example, a surface active agent, an animal fat or wax, e.g., lanolin, a mineral oil, e.g., liquid paraffin, a vegetable oil, e.g, peanut oil, oliver oil, corn oil or castor oil, or a polymer, e.g., a hydrocarbon polymer such as polyisobutene.

The surface active agents may comprise anionic compounds, for example, soaps, fatty sulphate esters, such as dodecyl sodium sulphate, fatty aromatic sulphonates, such as alkylbenzene sulphonates or butyl-naphthalene sulphonates, more complex fatty sulphonates, such as the amide condensation product of oleic acid and N-methyl taurine or the sodium sulphonate of dioctyl succinate.

The surface active agents may also comprise non-ionic surface active agents such as, for example, condensation products of fatty acids, fatty alcohols or fatty polyhydric alcohols, or the products obtained from the latter by condensation with ethylene oxide, or the products known as block copolymers of ethylene oxide and propylene oxide. The surface active agents may also comprise cationic agents such as, for example, cetyl trimethylammonium bromide.

The term "surface active agent" is used in the broad sense to cover materials variously called wetting agents, emulsifying agents and dispersing agents.

The composition may contain substances whose taste deters other animals from licking the composition off the animal treated. An example of such a substance is bitter aloes.

Generally, additives facilitating the use in pour-on formulations of other materials, e.g., systemic insecticides, active on animal physiology may be of use also in the present composition.

In general, in carrying out the method of the invention, the oral, parenteral or topical compositions described above may be administered to animals in a single does or divided into a plurality of smaller doses given over one or more days, for example, up to 14 days, to provide from about 1 to about 200 mg active compound per kilogram of animal body weight. It is preferred to employ in the range of 2.5–75 mg per kilogram of body weight.

If the compounds of the invention are to be employed against whipworm (Trichuris vulpis), it is preferred that such compounds be administered over a 5 to 9 day period in amounts ranging from about 4 to about 10 mg per kilogram of animal body weight per day, and more preferably over a 6 to about 8 day period in amounts ranging from about 4 to about 6 mg per kilogram of animal body weight per day.

If the compounds of the invention are to be employed against tapeworm, for example, *Taenia pisiformis* and *Dipylidium caninum*, it is preferred that such compounds be administered over a 2 to 10 day period, in amounts ranging from about 7 to about 20 mg per kilogram of animal body weight to provide from about 75 to about 400 mg per day and more preferably from about 8 to about 15 mg per kilogram of animal body weight to provide from about 100 to about 300 mg per day.

The following examples are provided for illustrative purposes and may include particular features of the invention, however the examples should be construed as limiting the invention, many variations of which are possible without departing from the spirit of scope thereof. All temperatues are in degrees centigrade.

EXAMPLE 1

[5-[[(2,2-Dichloro-1-methylcyclopropyl)methyl]thio]-1H-benzimidazol-2-yl]carbamic acid, methyl ester A. 1,1-Dichloro-2-chloromethyl-2-methylcyclopropane (Makosza and Fedorynski Synthesis, 1974, p. 2
Robinson, J. Org. Chem. 34, 2518 (1969))

To a vigorously stirred mixture of 45.3 g (0.5 mole) of 3-chloro-2-methylpropene, 120 g of chloroform (precursor of dichlorocarbene) and 1.5 g of benzyltriethylammonium chloride (TEBA) there is added dropwise 120 ml of 50% NaOH not allowing the temperature to rise above 40° C. The mixture is kept at 35 to 40° C for 3 hours then diluted with 250 ml of H$_2$O and extracted with chloroform. The organic layer is dried (MgSO$_4$) and the CHCl$_3$ removed invacuo. Distillation of the residue under house vacuum yields a fraction, b.p. 89–90° C, 45.7 g.

B. [5-[[(2,2-Dichloro-1-methylcyclopropyl)methyl]-thio]-1H-benzimidazol-2-yl]carbamic acid, methyl ester To a stirred mixture of 9.75 g (0.05 mole) of 2-nitro-4-thiocyanoaniline in 500 ml of absolute ethanol under N$_2$, there is added 2.1 g of sodium borohydride in portions. The mixture is stirred at room temperature for 15 minutes and the refluxed for 15 minutes. The heating mantle is removed and 3.25 g (0.05 mole) of KOH in 30 ml of absolute ethanol is added. The mixture is stirred for 1 minute. A solution of 8.7 g (0.05 mole) of 1,1-dichloro-2-chloromethyl-2-methylcyclopropane in 15 ml of absolute ethanol is added and the mixture is refluxed for 3 hours. Equal amounts of H$_2$O and CHCl$_3$ are added until two layers are formed. The organic layer is separated, dried (MgSO$_4$), and the solvent removed in vacuo to give a red oil which is triturated with 10 ml of absolute ethanol to yield 9.6 g of solid, m.p. 76–78° C.

A mixture of 9.0 g (0.03 mole) of 2-nitro-4-[(2,2-dichloro-1-methylcyclopropyl)methyl]thioaniline and 0.9 g of PtO$_2$ in 200 ml of absolute ethanol is reduced on the Parr hydrogenator at 50 psi until the theoretical amount of H$_2$ is absorbed. The mixture is filtered and the solvent is removed in vacuo to give a dark oil which is used immediately in the following reaction.

To a mixture of 6 g of 2-methyl-2-thiopseudourea sulfate in 6 ml of H$_2$O, there is added 5.7 ml of methylchloroformate at 0° C and the mixture is stirred for 15 minutes. Then there is added 14 ml of 25% NaOH dropwise and the mixture is stirred for 15 minutes. Then there is added 6 ml of acetic acid dropwise and the mixture is stirred for 15 minutes. Then the entire amount of the phenylenediamine from the preceding reaction in 20 ml of MeOH is added and the mixture is refluxed for 3 hours. The alcohol is removed in vacuo and H$_2$O is added. The resulting solid is filtered off and crystallized from MeCN to yield 4.9 g, m.p. 175–178°.

EXAMPLES 2 to 8

Following the procedure of Example 1A except substituting for 3-chloro-2-methylpropene, the compound shown in Column I of Table I below, and substituting for chloroform, the compound shown in Column II, the cyclopropane starting material shown in Column III is obtained.

TABLE I

| Ex. No. | Column I | Column II | Column III |
|---|---|---|---|
| | $HC{=}C-(CH_2)_m-\underset{R^3}{\overset{R^2}{C}}-(CH_2)_n-X$ with $R^4$ | $R^5\diagdown_{:C}\diagup R^6$ | $\underset{R^4}{\overset{R^5\diagdown\diagup R^6}{\triangle}}-(CH_2)_m-\underset{R^3}{\overset{R^2}{C}}-(CH_2)_n-X$ |
| 2. | $H_2C{=}\underset{CH_3}{\overset{CH_2CH_3}{C}}-CH-Cl$ | Cl$\diagdown_{:C}\diagup$Cl | Cl, Cl cyclopropane with C$_2$H$_5$, CH$_3$, CH—Cl |
| 3. | $H_2C{=}\underset{CH_3}{\overset{C_2H_5}{C}}-\underset{H}{\overset{}{C}}-Br$ | Cl$\diagdown_{:C}\diagup$Cl | Cl, Cl cyclopropane with C$_2$H$_5$, CH$_3$, CH—Br |
| 4. | $H_2C{=}\underset{C_2H_5}{\overset{CH_3}{C}}-\underset{CH_3}{\overset{}{C}}-Cl$ | Br$\diagdown_{:C}\diagup$Br | Br, Br cyclopropane with C$_2$H$_5$, CH$_3$, C—Cl |

TABLE I-continued

| Ex. No. | Column I: HC≡C—(CH₂)ₘ—C(R²)(R³)—(CH₂)ₙ—X (with R⁴) | Column II: R⁵R⁶C: | Column III: cyclopropane product |
|---|---|---|---|
| 5. | H₂C=C(C₃H₇)—(CH₂)₂—Br | Cl₂C: | 1,1-Cl₂-cyclopropane with —C(C₃H₇)—(CH₂)₂—Br |
| 6. | HC≡C(C₂H₅)—CH₂—Cl (H) | ClIC: | Cl,I-cyclopropane with —C(C₂H₅)—CH₂—Cl |
| 7. | HC≡C(C₆H₅)—CH₂—Br (H) | ClBrC: | Br,Cl-cyclopropane with —C(C₆H₅)—CH₂—Br |
| 8. | H₂C=C(CH₃)—CH₂—Cl | F₂C: | 1,1-F₂-cyclopropane with —C(CH₃)—CH₂—Cl |

Following the procedure of Example 1B except substituting for 1,1-dichloro-2-chloromethyl-2-methylcyclopropane the compound shown in Column III of Table I (Column I of Table II) below and substituting for methyl chloroformate the compound shown in Column II, the product shown in Column III is obtained.

TABLE II

Column I: cyclopropane—(CH₂)ₘ—C(R²)(R³)—(CH₂)ₙ—X  
Column II: HCOOR¹  
Column III: cyclopropane—(CH₂)ₘ—C(R²)(R³)—(CH₂)ₙ—S—benzimidazole-NHCO₂R¹

| Ex. No. | Column I (structure) | X | R¹ | Column III | R¹ |
|---|---|---|---|---|---|
| 2. | 1,1-Cl₂-cyclopropane-2-CH₃-2-CH(C₂H₅)— | Cl | n-C₃H₇ | as in Column I | as in Column II |
| 3. | 1,1-Cl₂-cyclopropane-2-CH₃-2-CH(C₂H₅)— | Br | C₂H₅ | | |
| 4. | 1,1-Br₂-cyclopropane-2-CH₃-2-C(C₂H₅)(CH₃)— | Cl | CH₂C₆H₅ | | |

| Ex. No. | Column I: cyclopropane—(CH₂)ₘ—C(R²)(R³)—(CH₂)ₙ— | X | R¹ | Column III: cyclopropane—(CH₂)ₘ—C(R²)(R³)—(CH₂)ₙ | R¹ |
|---|---|---|---|---|---|

TABLE II-continued

| # | Structure | | |
|---|---|---|---|
| 5. | Cl₂C(C₃H₇)—cyclopropyl—(CH₂)₂— | Br | CH₃ |
| 6. | Cl,I-C(C₂H₅)—cyclopropyl—CH₂— | Cl | C₂H₅ |
| 7. | Br,Cl-C(C₆H₅)—cyclopropyl—CH₂— | Br | C₂H₅ |
| 8. | F₂C(CH₃)—cyclopropyl—CH₂— | Cl | CH₃ |

(columns at right: as in Column I; as in Column II)

EXAMPLE 9

[5-[[(2,2-Dichloro-3-methylcyclopropyl)methyl]thio]-1H-benzimidazol-2-yl]carbamic acid, methyl ester A mixture of 21.6 g (0.3 mole) of crotyl alcohol, 600 ml of 50% aqueous sodium hydroxide and 1.2 g of triethylbenzylammonium chloride (TEBA) is stirred vigorously at 40° C to emulsify. Then 480 ml of chloroform is added dropwise over 2 hours and the mixture is stirred for a further 2 hours. The mixture is poured into water and extracted with chloroform. The organic layers are combined, dried (MgSO₄), and the solvent is removed in vacuo. Distillation of the residue yields 18.3 g of 1-chloromethyl-2,2-dichloro-3-methylcyclopropane.

To a stirred mixture of 9.75 g (0.05 mole) of 2-nitro-4-thiocyanoaniline in 200 ml of dry acetonitrile under nitrogen there is added 2.1 g (0.05 mole) of sodium borohydride in portions. The mixture is stirred at room temperature for 15 minutes and then refluxed for 15 minutes. The heating mantle is removed and 3.5 g (0.05 mole) of KOH is added. The mixture is stirred for 15 minutes. Then a solution of 8.7 g (0.05 mole) of 1-chloromethyl-2,2-dichloro-3-methylcyclopropane in 10 ml of acetonitrile is added and the mixture is refluxed for 2 hours. The reaction mixture is cooled, filtered, and the solvent is removed in vacuo. Water and chloroform are added to the residue. The organic layer is separated, dried (MgSO₄), and the solvent is removed in vacuo to give 12.4 g of red orange oil.

A mixture of 12 g (0.04 mole) of the above nitroaniline and 1.2 g PtO₂ in 200 ml of absolute ethanol is reduced on the Parr hydrogenator at 50 psi. The mixture is filtered and the solution is used immediately in the following reaction.

To the above solution there is added 8.1 g of 1,3-bis(-methoxycarbonyl)-5-methylisothiourea and 0.5 ml of acetic acid and the mixture is refluxed for 3 hours. The solvent is removed in vacuo and water is added. The resulting solid is filtered off and crystallized from ethanol to yield 6.2 g of the title compound.

EXAMPLE 10

Oral Formulation of [5-[[(2,2-Dichloro-1-methylcyclopropyl)-methyl]thio]-1H-benzimidazol-2-yl]carbamic acid, methyl ester Medication suitable for oral administration is prepared by filling gelatin capsules with suitable amounts of [5-[[(2,2-dichloro-1-methylcyclopropyl)methyl]-thio-1H-benzimidazol-2-yl]carbamic acid, methyl ester.

EXAMPLE 11

Testing of Oral Formulation of [5-[[(2,2-Dichloro-1-methylcyclopropyl)methyl]thio]-1H-benzimidazol-2-yl]carbamic acid, methyl ester The following test is carried out to determine the effectiveness of treating dogs naturally infected with whipworm (*Trichuris vulpus*) and tapeworms (*Taenia pisiformis* and *Dipylidium caninum*) by orally administering capsules containing [5-[[(2,2-dichloro-1-methylcyclopropyl)methyl]thio]-1H-benzimidazol-2-yl]carbamic acid, methyl ester prepared in Example 1.

The dogs are fasted overnight and receive medication the following morning.

Total fecal collections are made from each dog daily for seven days following treatment. Daily fecal material is soaked in water and washed through a 40-mesh sieve using a water spray and all scolices, strobilae, proglottids and nematodes, immatures and adults are recovered.

Seven days after medication, the dogs are euthanitized and intestines and cecum are removed and examined for tapeworms and whipworms. the intestinal contents are mucosal scrapings are washed through a 40-mesh sieve prior to examination for tapeworms (scolices) and whipworm under the dissection microscope.

A first group of dogs receiving 5 mg/kg for 7 days of [5-[[(2,2-dichloro-1-methylcyclopropyl)methyl]thio]-1H-benzimidazol-2-yl]carbamic acid, methyl ester is found to have a 93% reduction in whipworms.

In a Control A experiment, one group of dogs receiving 5 mg/kg for 7 days of [5-[[(2,2-dichlorocyclopropyl)methyl]thio]-1H-benzimidazol-2-yl]carbamic acid, methyl ester is found to have only a 16% reduction in whipworms.

A second group of dogs receiving 100 mg twice daily for 5 days of [5-[[(2,2-dichloro-1-methylcyclopropyl)methyl]thio]-1H-benzimidazol-2-yl]carbamic acid, methyl ester is found to have a 100% reduction in *Taenia pisiformis* and a 50% reduction in *Dipylidium caninum*.

In a Control B experiment, one group of dogs receiving 100 mg twice daily for 5 days of [5-[[(2,2-dichlorocyclopropyl)methyl]thio]-1H-benzimidazol-2-yl]carbamic acid, methyl ester is found to have a 0% reduction in the tapeworms *Taenia* and *Dipylidium caninum*.

A third group of dogs receiving 25 mg/kg for 5 days of [5-[[(2,2-dichloro-1-methylcyclopropyl)methyl]thio]-1H-benzimidazol-2-yl]carbamic acid, methyl ester is found to have a 100% reduction in whipworms, a 100% reduction in i Taenia pisiformis and a 100% reduction in *Dipylidium caninum*.

In a Control C experiment, one group of dogs receiving 25 mg/kg for 5 days of [5-[[(2,2-dichlorocyclopropyl)methyl]thio]-1H-benzimidazol-2-yl]carbamic acid, methyl ester is found to have only a 34% reduction in whipworms and a 0% reduction in the tapeworms *Taenia pisiformis* and *Dipylidium caninum*.

The above test results clearly show the surprising superiority of [5-[[(2,2-dichloro-1-methylcyclopropyl)methyl]thio]-1H-benzimidazol-2-yl]carbamic acid, methyl ester over [5-[[(2,2-dichlorocyclopropyl)methyl]thio]-1H-benzimidazol-2-yl]carbamic acid, methyl ester in treatment or prevention of whipworm and tapeworm.

What is claimed is:

1. A compound of the structure

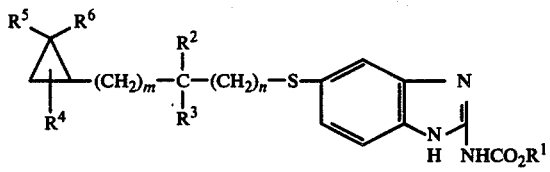

wherein $R^1$ is lower alkyl or phenyl-lower alkyl, $R^2$ and $R^3$ are the same or different and are hydrogen or lower alkyl, $R^4$ is lower alkyl or phenyl, and $R^5$ and $R^6$ are the same or different and are chlorine, bromine, fluorine or iodine, m is 0 to 3, n is 0 to 3, and m + n is $\leq$ 5, and physiologically acceptable salts thereof.

2. The compound as defined in claim 1 wherein $R^1$ is lower alkyl or benzyl.

3. The compound as defined in claim 1 wherein $R^2$ and $R^3$ are the same or different and are hydrogen or methyl.

4. The compound as defined in claim 1 wherein m is 0, n is 0, and $R^2$ and $R^3$ are hydrogen and $R^4$ is in the 1-position.

5. The compound as defined in claim 1 wherein $R^5$ and $R^6$ are chlorine or bromine and $R^4$ is lower alkyl in the 1-position.

6. The compound as defined in claim 1 having the name [5-[((2,2-dichloro-1-methylcyclopropyl)methyl]-thio]-1-H-benzimidazol-2-yl]carbamic acid, methyl ester.

7. A parmaceutical composition for use in treating or preventing tapeworm or whipworm comprising a therapeutically effective amount of a compound as defined in claim 1 and a pharmaceutically acceptable carrier therefor.

8. A method for treating or preventing tapeworm or whipworm in a mammalian or poultry host, which comprises administering to a host a therapeutically effective amount of the composition as defined in claim 7.

9. The method as defined in claim 8 wherein the compound present in said composition has the name [5-[[(2,2-dichloro-1-methylcyclopropyl)methyl]thio]-1H-benzimidazol-2-yl]carbamic acid, methyl ester.

10. The method as defined in claim 8 wherein said tapeworm is of the species *Taenia pisiformis*.

11. The method as defined in claim 8 wherein said tapeworm is of the species *Dipylidium caninum*.

12. The method as defined in claim 7 wherein said composition is administered over a 2 to 10 day period to provide compound in amounts ranging from about 7 to about 20 mg/kg/day to provide from about 25 to about 400 mg/day in the treatment of tapeworm.

13. The method as defined in claim 7 wherein said composition is administered over a 5 to 9 day period to provide compound in amounts ranging from about 4 to about 10 mg/kg/day in the treatment of whipworm.

14. The method as defined in claim 8 wherein said whipworm is of the species *Trichuris vulpis*.

15. A method for treating or preventing helminthiasis, which comprises administering to a host a therapeutically effective amount of the composition as defined in claim 7.

UNITED STATES PATENT AND TRADEMARK OFFICE
CERTIFICATE OF CORRECTION

PATENT NO. : 4,138,493
DATED : February 6, 1979
INVENTOR(S) : Rudiger D. Haugwitz et al.

It is certified that error appears in the above-identified patent and that said Letters Patent are hereby corrected as shown below:

```
Column 1, line 49, "5(6" should read --5(6)--.
Column 7, line 23, after "should" and before "be" insert
   --not--.
Column 7, line 25, "of" should read --or--.
Column 8, line 9, "the" should read --then--.
Columns 9 and 10, at the bottom, the column headings for
   Columns I, II and III should be inserted at the top of
   Columns 11 and 12, before Examples 5 to 8.
Column 11, line 37, "ihto" should read --into--.
Column 12, line 56, "the" should read --The--.
Column 12, line 57, "are" should read --and--.
Column 13, line 17, before "Taenia" delete "i".
Column 13, line 30, after "in" insert --the--.
```

Signed and Sealed this

Twenty-ninth Day of May 1979

[SEAL]

Attest:

RUTH C. MASON
Attesting Officer

DONALD W. BANNER
Commissioner of Patents and Trademarks